United States Patent
Liu et al.

(10) Patent No.: US 9,015,882 B2
(45) Date of Patent: Apr. 28, 2015

(54) TRANSFORMABLE BED FOR EXAMINATIONS IN PEDIATRIC OPHTHALMOLOGY

(75) Inventors: Yizhi Liu, Guangzhou (CN); Haotian Lin, Guangzhou (CN); Weirong Chen, Guangzhou (CN); Lixia Luo, Guangzhou (CN)

(73) Assignee: Zhongshan Ophthalmic Center, SYSU, Guangzhou (CN)

( * ) Notice: Subject to any disclaimer, the term of this patent is extended or adjusted under 35 U.S.C. 154(b) by 540 days.

(21) Appl. No.: 13/434,191

(22) Filed: Mar. 29, 2012

(65) Prior Publication Data

US 2013/0074265 A1 Mar. 28, 2013

(30) Foreign Application Priority Data

Jul. 15, 2011 (CN) .......................... 2011 2 0251679

(51) Int. Cl.

| | |
|---|---|
| *A61G 13/12* | (2006.01) |
| *A61G 13/00* | (2006.01) |
| *A61G 13/08* | (2006.01) |
| *A61B 3/00* | (2006.01) |
| *A61G 13/10* | (2006.01) |
| *A61G 15/02* | (2006.01) |
| *A61G 1/017* | (2006.01) |

(Continued)

(52) U.S. Cl.
CPC ............ *A61G 13/0018* (2013.01); *A61G 13/08* (2013.01); *A61G 1/017* (2013.01); *A61G 1/0237* (2013.01); *A61G 1/044* (2013.01); *A61B 3/0083* (2013.01); *A61G 13/104* (2013.01); *A61G 15/02* (2013.01); *A61G 2200/14* (2013.01); *A61G 2200/32* (2013.01); *A61G 2200/34* (2013.01)

(58) Field of Classification Search
CPC ...................................... A61G 5/006
USPC ............ 5/600, 603, 613, 621, 624, 86.1, 655; 297/141, 142, 174 R, 174 CS
See application file for complete search history.

(56) References Cited

U.S. PATENT DOCUMENTS

| | | | | |
|---|---|---|---|---|
| 1,749,867 | A | * | 3/1930 | Allison .............................. 5/618 |
| 2,821,241 | A | * | 1/1958 | Schwahn ....................... 297/141 |
| 4,361,916 | A | * | 12/1982 | McDaniel ......................... 5/603 |

(Continued)

FOREIGN PATENT DOCUMENTS

| | | |
|---|---|---|
| CN | 2331344 Y | 8/1999 |
| CN | 2686583 Y | 3/2005 |

(Continued)

*Primary Examiner* — Michael Trettel
(74) *Attorney, Agent, or Firm* — Westerman, Hattori, Daniels & Adrian, LLP

(57) ABSTRACT

A transformable bed for examinations in pediatric ophthalmology, especially suitable for the use of general anesthesia when conducting eye examinations, is provided. The bed may include a fixed bed board, a movable bed board, a movable seat, a movable support, a securing strap, and a main frame. The bed may be fixedly connected to the top of the main frame, the movable bed board may be rotationally connected to the top of the main frame, and the movable seat may be rotationally connected to the top of the main frame. The securing strap may be disposed on the movable bed board, in which one end of the movable support may be removably connected to the movable bed board, and another end may be removably connected to the main frame. The transformable bed may function both as an anesthesia bed and a handcart, and may be quickly switched therebetween.

5 Claims, 3 Drawing Sheets

(51) Int. Cl.
*A61G 1/02* (2006.01)
*A61G 1/044* (2006.01)

(56) References Cited

U.S. PATENT DOCUMENTS 4,658,450 A      4/1987    Thompson
4,685,159 A  *   8/1987    Oetiker ............................ 5/608
4,862,530 A  *   9/1989    Chen ................................. 5/618
6,691,349 B2 *   2/2004    Blevins ............................ 5/613
7,127,757 B2 *  10/2006    Roberto ........................... 5/613

FOREIGN PATENT DOCUMENTS

CN          201104968 Y      8/2008
CN          201719469 U      1/2011

* cited by examiner

TRANSFORMABLE BED FOR EXAMINATIONS IN PEDIATRIC OPHTHALMOLOGY

CROSS-REFERENCE TO RELATED APPLICATION

The present application claims priority from Chinese Patent Application No. CN 201120251679.3 filed on Jul. 15, 2011, the disclosure of which is hereby incorporated herein by reference.

TECHNICAL FIELD

The present utility model concerns the technical field of medical devices, and specifically relates to an transformable bed that can be used for examinations in pediatric ophthalmology

BACKGROUND ART

For a long period of time, specialist examinations of pediatric ophthalmological diseases have always been a challenge for the ophthalmological field, both domestically and abroad. Child patients who do not cooperate with the ophthalmological examinations have posed great difficulty in the treatment of ophthalmological diseases. Currently, pediatric ophthalmologists overseas primarily recommend examination under anesthesia (EUA) to resolve this difficulty. However, EUA poses new problems for pediatric ophthalmologists. This is because the majority of ophthalmological examination equipment being used clinically is desktop equipment, which requires the examinee to be seated with his or her body upright, head secured on the headrest of the desktop equipment, and jaw secured on the adjustable jawrest, adjusting the up and down button to situate the examinee's eyes at the best examination position. However, in an anesthetized state, the best anesthetized position for a patient is a supine position. If an accident occurs under anesthesia, the patient must immediately be laid down in order to implement the necessary emergency measures. When a child patient in an anesthetized state is examined with desktop equipment, the way that this used to be done was to have a parent or anesthesiologist hold the child patient and get the child patient's head to rest on the headrest and the jawrest, and then use a eye speculum to open the eyelid and conduct the examination. If an accident occurred under anesthesia and the child patient need to be treated with emergency medication, then the parent or anesthesiologist would have to hold the child patient on the anesthesia bed in order that the child patient be able to lie supine.

There are two drawbacks of the traditional method: first, when the child patient is held in order to conduct the examination, the child patient's chest and abdominal area are likely to be compressed, which will cause difficulty breathing, and it is difficult for the parent or anesthesiologist to cooperate and meet the requirements needed for the head height, the front and back, and the position to be secured during the eye examination; second, once an accident occurs under anesthesia, the child patient cannot immediately lie supine, and the life of the child patient is thus seriously threatened.

CONTENT OF THE UTILITY MODEL

In view of the above, there is a necessity to provide a transformable bed for examinations in pediatric ophthalmology that can function both as an anesthesia bed and a handcart, in order to resolve the foregoing issues.

A transformable bed for examinations in pediatric ophthalmology, comprising a fixed bed board, a movable bed board, a movable seat, a movable support, a securing strap, and a main frame, where the fixed bed board is fixedly connected to the top of the main frame, the movable bed board is rotationally connected the top of the main frame, the movable seat is rotationally connected to the top of the main frame, the securing strap is disposed on the movable bed board, one end of the movable support can be removably connected to the movable bed board, and the other end can be removably connected to the main frame.

The transformable bed for examinations in pediatric ophthalmology, wherein the bottom of the main frame is further equipped with omnidirectional wheels.

The transformable bed for examinations in pediatric ophthalmology, wherein the movable seat comprises an L shaped frame, armrests for the seat, an adjustable handle for the seat, an movable seat surface, and an adjustable support for the seat, where the adjustable support for the seat is disposed on the L shaped frame, the movable seat surface is disposed on the adjustable support for the seat, the adjustable handle for the seat and the adjustable support for the seat are rotationally connected, and the armrests for the seat can be disassembled and arranged at one end of the L shaped frame.

The transformable bed for examinations in pediatric ophthalmology, wherein the adjustable support for the seat is a simple hoisting jack.

The transformable bed for examinations in pediatric ophthalmology, wherein the securing strap is a hook and loop fastener.

The current utility model can function as both an anesthesia bed and a handcart, and can be quickly switched therebetween, thus allowing the child patient being anesthetized to be swiftly switched between a supine position and an upright seated position. When being used as a handcart, it can be used for child patients under general anesthesia or those in a conscious state. Through the use of omnidirectional wheels, the child patient seated in the fixed seat can be nimbly switched between different desktop examination equipment. The relative position between the child patient and the examination equipment can be quickly adjusted, which is especially suitable for the requirements of multiple examinations. The height of the seat for child patients may be adjusted freely and quickly by means of the movable seat, and the range of height fully complies with the height requirements for various types of desktop equipment currently used in ophthalmological examinations. When the child patient is in the seated position, the torso may be secured with the securing strap and the armrests of the chair, which is quite stable and safe, while the head remains mobile, not only serving the requirements of the head position dictated by the examination equipment but also facilitating unimpeded breathing.

DESCRIPTION OF ATTACHED DRAWINGS

SPECIFIC EMBODIMENTS

Figure 1:
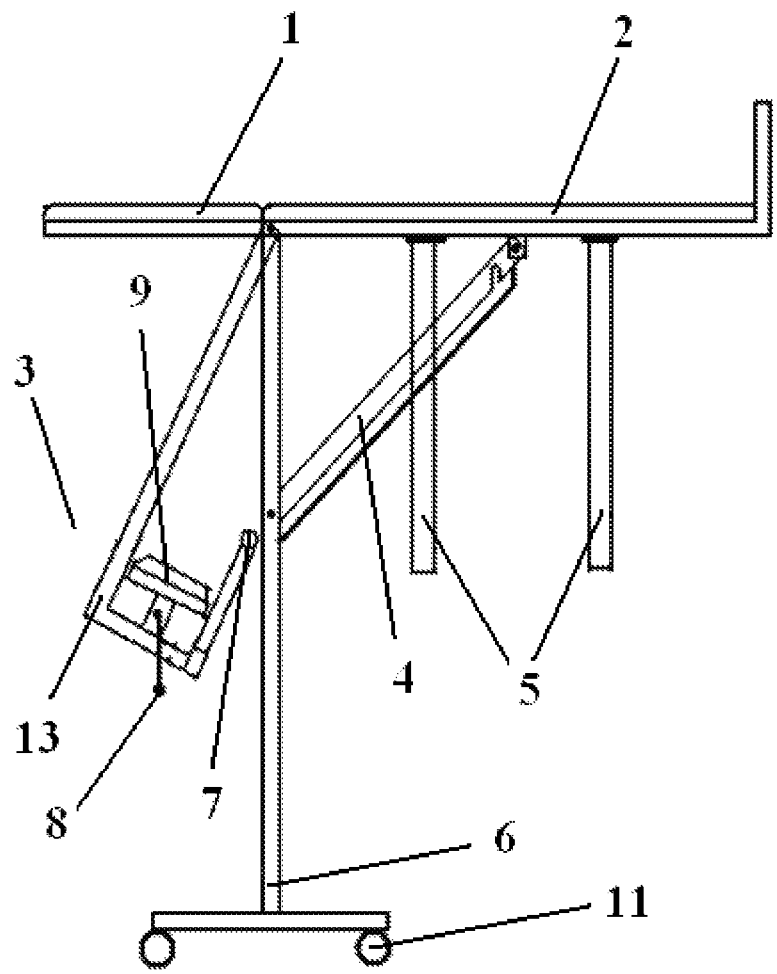
FIG. 1 is an illustration of the current utility model used as an anesthesia bed.
Figure 2:
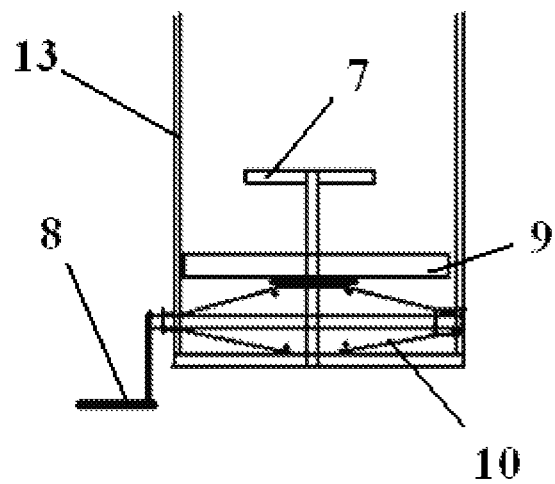
FIG. 2 is an illustration of the movable seat from FIG. 1.

Referring to FIG. 1 and FIG. 2, the current utility model is a transformable bed used for examinations in pediatric ophthalmology, which is especially convenient for ophthalmological examinations when general anesthesia is administered, comprising a fixed bed board (1), a movable bed board (2), a movable seat (3), a movable support (4), a securing strap (5) (high quality hook and loop strap), and a main frame (6). The main frame (6) is used to support the entire transformable bed. The fixed bed board (1) is fixedly connected to the top of the main frame (6), the movable bed board (2) is rotationally connected to the top of the main frame (6), the movable seat (3) is rotationally connected to the top of the main frame (6), the securing strap (5) is disposed on the movable bed board (2), where two high quality securing straps (5) are preferably used at the top and at the bottom.

One end of the movable support (4) can be removably connected to the movable bed board (2), and the other end can be removably connected to the main frame (6).

The bottom of the main frame (6) is further fitted with omnidirectional wheels (11).

The movable seat (3) comprises an L shaped frame (13), armrests for the seat (7), an adjustable handle for the seat (8), a movable seat surface (9), and an adjustable support for the seat (10) (i.e. the simple hoisting jack); the adjustable support for the seat (10) is disposed on the L shaped frame (13), the movable seat surface (9) is disposed on the adjustable support for the seat (10), and the adjustable handle for the seat (8) and the adjustable support for the seat (10) are rotationally connected. Through rotating the adjustable handle for the seat (8), the height of the adjustable support for the seat (10) can be controlled, thereby elevating or lowering the movable seat surface (9). The armrests for the seat (7) can be disassembled and arranged at the end of the L shaped frame (13) close to the movable seat surface (9).

When in actual use, the movable seat (3) is turned counterclockwise to the seven o'clock position as shown in FIG. 1, one end of the movable support (4) is connected to the movable bed board (2), and the other end is connected to the main frame (6); when the fixed bed board (1) and the movable bed board (2) are in the level position, a regular anesthesia bed is thus constituted.

Figure 3:
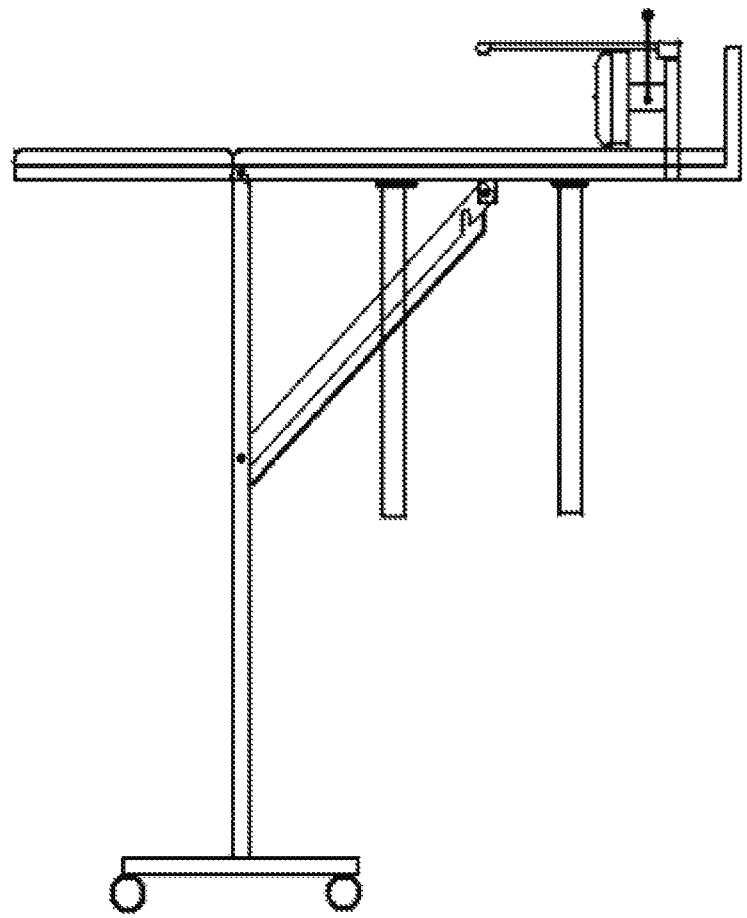
FIG. 3 is an illustration of the process of the utility model being switched from an anesthesia bed to a handcart.
Figure 4:
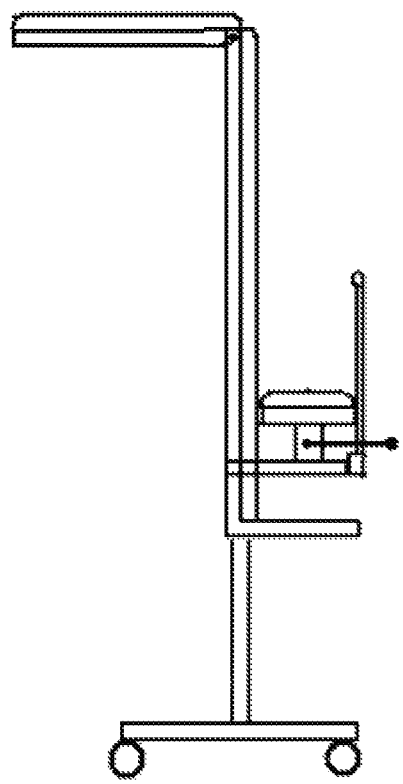
FIG. 4 is an illustration of the current utility model used as a handcart.

Referring to FIG. 3 and FIG. 4, the movable seat (3) is turned clockwise to the level position, and then the torso of the child under anesthesia is laid supine on the movable bed board (2) and his or her bottom seated on the movable seat surface (9). The two securing straps (5) at the top and bottom are used to secure the child's body. The armrests (7) of the seat are inserted; finally, the movable support (4) is removed, and the movable bed board (2), the movable seat (3), and the secured child patient are all simultaneously turned clockwise from the level position to the upright position, whereupon the entire device becomes a handcart that can maintain the anesthetized child patient in an upright position.

When being used as a handcart, the fixed bed board (1) is used as a handle for the same; by virtue of the omnidirectional wheels (11), the child patient who is in a secured seated position can be conveniently moved around between different desktop examination equipment. The height of the child patient's seat may be quickly and freely adjusted in both directions by means of the adjustable handle for the seat (8), so that the adjustable support for the seat (10) can be quickly elevated or lowered, similar to the mechanism of a hoisting jack. This ensures that the child patient on the movable seat surface (9) can meet the differing height requirements of various types of desktop examination equipment currently used in ophthalmology and allow use for a child patient under general anesthesia or in a conscious state. The current utility model can quickly adjust the relative position between the child patient and the examination equipment, and is particularly suited to the needs of quickly completing multiple examinations.

The current utility model allows the movable bed board (2) and the movable seat (3) to be quickly and simultaneously rotated, and to be switched between the level position and the upright position by providing two options for the movable support (4): being engaged or being removed. This ensures that the position needed for the child patient in an anesthetized state, either lying supine or sitting upright, can be quickly selected.

When the child patient is in an upright position, his or her torso is secured by the securing straps (5) and the armrests for the seat (7), and is quite secure and safe. Meanwhile, the head of the child patient remains mobile, which not only serves the requirements for head position dictated by the examination equipment, but also ensures unimpeded breathing.

When the child patient must be switched to a supine position, the securing straps (5) and the armrests for the seat (7) used to secure the body are quickly removed, and the movable seat (3) can also be quickly turned counterclockwise to the seven o'clock position under the bed; when the fixed bed board (1) and the movable bed board (2) are in a level position, a standard anesthesia bed is formed.

The current utility model can function both as an anesthesia bed and a handcart, and can be quickly switched therebetween, thus allowing the child patient under anesthesia to be swiftly switched between a supine position and an upright seated position. When being used as a handcart, it can be used for child patients under general anesthetic or those in a conscious state; through the use of omnidirectional wheels, the child patient seated in the fixed seat can be nimbly switched between different desktop examination equipment. The relative position between the child patient and the examination equipment can be quickly adjusted, which is particularly suited to the requirements of multiple examinations. The height of the seat for child patients may be adjusted freely and quickly by means of the movable seat, and the range of height fully complies with the height requirements for various types of desktop equipment currently used in ophthalmological examinations. When the child patient is in the seated position, the torso may be secured with the securing strap and the armrests of the chair, which is quite stable and safe, while the head remains mobile, not only serving the head position requirements dictated by the examination equipment, but also facilitating unimpeded breathing, while at the same time increasing the efficiency and safety of examinations.

The research and development of this utility model and the expenses incurred during the patent application process were sponsored by the Ministry of Health (Administration) Hospital 2010-2012, critical clinical project "The Influence of Timing and Method of Operation on the Long Term Effects of Treatment of Congenital Cataracts" (project number: 175).

The examples mentioned above serve only to demonstrate some embodiments of the current utility model; the descriptions therein are specific and detailed but should not be construed as limitations on the claimed scope of the current utility model. It should be noted that persons of ordinary skill in the art could make certain modifications and improvements without deviating from the ideas of the present utility model; these shall all fall under the scope of protection of the current utility model. Therefore, the scope of protection of the patent for the current utility model shall be based upon the appended claims.

The invention claimed is:

1. A transformable bed for examinations in pediatric ophthalmology, characterized in comprising a fixed bed board, a movable bed board, a movable seat, a movable support, a securing strap, and a main frame, where the fixed bed board is fixedly connected to a top of the main frame, the movable bed board is rotationally connected the top of the main frame, the movable seat is rotationally connected to the top of the main frame, the securing strap is disposed on the movable bed board, one end of the movable support can be removably connected to the movable bed board, and the other end can be removably connected to the main frame.

2. The transformable bed for examinations in pediatric ophthalmology as described in claim 1, characterized in that a bottom of the main frame is further equipped with omnidirectional wheels.

3. The transformable bed for examinations in pediatric ophthalmology as described in claim 1, characterized in that the movable seat comprises an L shaped frame, armrests for the seat, an adjustable handle for the seat, a movable seat surface, and an adjustable support for the seat, where the adjustable support for the seat is disposed on the L shaped frame, the movable seat surface is disposed on the adjustable support for the seat, the adjustable handle for the seat and the adjustable support for the seat are rotationally connected, and the armrests for the seat can be disassembled and arranged at one end of the L shaped frame.

4. The transformable bed for examinations in pediatric ophthalmology as described in claim 3, characterized in that the adjustable support for the seat is a simple hoisting jack.

5. The transformable bed for examinations in pediatric ophthalmology as described in patent claim 1, characterized in that the securing strap is a hook and loop fastener.

\* \* \* \* \*